(12) United States Patent
Nakazawa et al.

(10) Patent No.: US 11,426,064 B2
(45) Date of Patent: Aug. 30, 2022

(54) PERIMETER FOR TESTING FOR PROGRESSION OF GLAUCOMA

(71) Applicants: Tohoku University, Miyagi (JP); Kowa Company, Ltd., Aichi (JP)

(72) Inventors: Toru Nakazawa, Miyagi (JP); Satoshi Shimada, Tokyo (JP); Takuya Hara, Tokyo (JP)

(73) Assignees: Tohoku University; Kowa Company, LTD

( * ) Notice: Subject to any disclaimer, the term of this patent is extended or adjusted under 35 U.S.C. 154(b) by 171 days.

(21) Appl. No.: 16/633,548

(22) PCT Filed: Jul. 23, 2018

(86) PCT No.: PCT/JP2018/027442
§ 371 (c)(1),
(2) Date: Jan. 23, 2020

(87) PCT Pub. No.: WO2019/021986
PCT Pub. Date: Jan. 31, 2019

(65) Prior Publication Data
US 2020/0205655 A1    Jul. 2, 2020

(30) Foreign Application Priority Data
Jul. 24, 2017 (JP) .............................. JP2017-142538

(51) Int. Cl.
*A61B 3/024* (2006.01)
*A61B 3/00* (2006.01)
*A61B 3/06* (2006.01)

(52) U.S. Cl.
CPC ............ *A61B 3/024* (2013.01); *A61B 3/0016* (2013.01); *A61B 3/063* (2013.01)

(58) Field of Classification Search
CPC .................................................... A61B 3/24
USPC .......................................................... 351/224
See application file for complete search history.

(56) References Cited

U.S. PATENT DOCUMENTS

| | | | | |
|---|---|---|---|---|
| 5,461,435 A * | 10/1995 | Rootzen | ............... | A61B 3/024 351/222 |
| 5,463,431 A * | 10/1995 | Suzuki | ............... | A61B 3/024 351/222 |
| 6,527,391 B1 * | 3/2003 | Heijl | ............... | A61B 3/024 351/243 |
| 7,309,129 B2 * | 12/2007 | Suzuki | ............... | A61B 3/024 351/206 |
| 7,325,925 B1 * | 2/2008 | Shimada | ............... | A61B 3/024 351/206 |

(Continued)

OTHER PUBLICATIONS

Antonio Ferreras, Lúis E. Pablo, David F. Garway-Heath, Paolo Fogagnolo, Julián Garćia-Feijoo; Mapping Standard Automated Perimetry to the Peripapillary Retinal Nerve Fiber Layer in Glaucoma. Invest. Ophthalmol. Vis. Sci. 2008;49(7):3018-3025 (Year: 2008).*

(Continued)

*Primary Examiner* — Zachary W Wilkes
(74) *Attorney, Agent, or Firm* — Richard P. Gilly, Esquire; Archer & Greiner

(57) ABSTRACT

In examining a patient for progression of glaucoma, a perimeter capable of appropriately assessing visual field progression in a short period of time, therefore lessening the physical burden of testing on the examinee.

7 Claims, 9 Drawing Sheets

(56) References Cited

U.S. PATENT DOCUMENTS

| | | | | |
|---|---|---|---|---|
| 7,475,988 B2 * | 1/2009 | Shimada | ................ | A61B 3/024 |
| | | | | 351/224 |
| 7,773,769 B2 * | 8/2010 | Rattan | ...................... | A61B 3/06 |
| | | | | 382/100 |
| 8,210,681 B2 * | 7/2012 | Flanagan | ............... | A61B 5/163 |
| | | | | 351/209 |
| 9,155,464 B2 * | 10/2015 | Tanaka | ................... | A61B 3/024 |
| 9,622,653 B2 * | 4/2017 | Hara | ...................... | A61B 3/024 |
| 9,808,149 B2 * | 11/2017 | Gonzalez de la Rosa | .................. | |
| | | | | A61B 3/12 |
| 9,826,897 B2 * | 11/2017 | Shimada | .............. | A61B 3/0025 |
| 9,861,276 B2 * | 1/2018 | Crabb | ................... | A61B 3/024 |
| 9,883,793 B2 * | 2/2018 | Benner | ............... | A61B 3/0025 |
| 11,076,757 B2 * | 8/2021 | Rotenstreich | .......... | A61B 3/024 |
| 2018/0014724 A1 * | 1/2018 | Wroblewski | ......... | A61B 3/0025 |

OTHER PUBLICATIONS

Carl Zeiss Meditec Inc. Humphrey Field Analyzer II-i Series, Carl Zeiss Meditec Inc., 2010 (Year: 2010).*

* cited by examiner

TOTAL DEVIATION AND PATTERN DEVIATION

PERIMETER FOR TESTING FOR PROGRESSION OF GLAUCOMA

TECHNICAL FIELD

This invention relates to a perimeter capable of detecting a progress of visual field abnormality in associated with Glaucoma Optic Neurosis in a short period, reducing burdens on an examinee.

BACKGROUND ART

In a perimetry (threshold testing), it is possible to measure the light sensitivity at each retina part, and it is possible to assess visual field progression in glaucoma by confirming the change of such a sensitivity over time.

In the perimetry, while fixating some point, the examinee responds whether the examinee can perceive luminous points having various brightness presented in sequence on measurement points that are set on a periphery of some point. In the perimetry to be usually conducted, 54 through 76 measurement points are located, and it takes 3 to 15 minutes or so for one eye for such a perimetry, so that a heavy burden is imposed on the examinee.

The Glaucoma that is a main target for the perimetry is the Glaucoma Optic Neurosis that is the visual field abnormality due to disappearance of progressive retinal ganglion cells. Therefore, it is necessary to detect a presence of the visual field abnormality and its degree as quickly as possible and to give a proper medical treatment.

But, such a perimetry imposes a big burden on the examinee as mentioned above, and for this reason the perimetry is done at almost semiannual frequency.

SUMMARY OF INVENTION

Problems to be Solved by Invention

But, it is difficult to quickly assess the visual field progression at such a frequency, and a timing of appropriate treatment may be lost.

An object of the invention is to provide a perimeter capable of appropriately assessing the visual field progression in a short period, restricting the burden on the examinee.

Means for Solving Problems

The first aspect of the invention is a perimeter (2) capable of acquiring, as a threshold (SV), a value corresponding to a response result of an examinee (22) to an stimulus presented with various brightness, for a first number (54 or 72) of measurement points set across an entire measurement visual field of the ocular fundus of a subject eye (22a), displaying the threshold as a map image (MAP1) of a threshold testing result (SHR) on a display (20) and storing the same in a memory (13); comprising:

a pattern deviation calculator (15) that obtains a pattern deviation (PDV) of the threshold (SV) relating to each measurement point (RG), from the threshold testing result (SHR);

a probability map producer (15) that obtains a P value representing the obtained pattern deviation (PDV) for each measurement point (RG) as a probability variable, and generates a probability map image (MAP4) of a pattern probability plot (PDP) indicating the measurement points (RG) for the respective P values;

a measurement point selector (16) that selects, from an abnormal measurement point group of points in the probability map image (MAP4) in which at least a prescribed number of measurement points (RG) (3 points) having a P value that is a first prescribed value (5%) or lower are continuous, and, of those, at least one point has the P value that is a second prescribed value (1%) or lower, smaller than the first prescribed value (5%), measurement points to be used as subsequent measurement points, until a prescribed number of points (10 points) have been reached; and a memory (13) that stores the subsequent measurement points selected through the measurement point selector (16), wherein the selection of the subsequent measurement points through the measurement point selector (16) is controlled in such a way that the measurement points (RG) are selected from ones comprising the abnormal measurement point group in order of those having a better pattern deviation (PDV).

The second aspect of the invention is the perimeter (2), further comprising:

an input portion (19) through which an identification code (ID and the like) on the subject eye (22a) can be inputted, and a re-inspection measurement point output portion (11) that, when the identification code is inputted in the input portion (19), reads the subsequent measurement points for the subject eye (22a) corresponding to the identification code out of the memory (13) and outputs the read out to an output portion (20).

The third aspect of the invention is the perimeter, wherein the memory (13) stores a sector figure (SEC) that shows sectors formed by dividing the visual field to be measured so as to correspond to a running direction of retina nerve fibers, and the measurement point selector (16) has a sector extractor (16), the sector extractor reads and refers to the sector figure (SEC) stored in the memory (13) when the number of selecting the subsequent measurement points through the measurement point selector does not reach the prescribed number, and extracts, from the measurement points (RG) excluding the measurement points (RG) comprising the abnormality measurement point group in the sectors (SC1, SC2, SC3, SC4, SC5, SC6) to which the measurement points (RG) already measured belong, the subsequent measurement points in the order of the worse pattern deviation till the extracted number of measurement points reaches the prescribed number.

The fourth aspect of the invention is the perimeter, wherein the prescribed number is 10.

The fifth aspect of the invention is the perimeter, the measurement point selector (16) has a map image selector (16), when the number of selecting the subsequent measurement points through the measurement point selector (16) does not reach the prescribed number, the map image selector selects the measurement point (RG) close to the abnormality measurement point group in the probability map image (MAP4) of the pattern deviation probability plot (PDP) as the subsequent measurement points.

The sixth aspect of the invention is the perimeter, wherein the measurement point selector (16) selects, from the abnormality measurement point group in the probability map image (MAP4), the measurement points in which at least a prescribed number of measurement points having P value that is 5% or lower are continuous, and of those at least one have the P value that is 1% or lower as the subsequent measurement points.

The seventh aspect of the invention is the perimeter, wherein the measurement point selector (16) selects, from the abnormality measurement point group in the probability map image (MAP4), the measurement points in which at least three measurement points having P value that is 5% or lower are continuous, and of those at least one have the P value that is 1% or lower as the subsequent measurement points.

Effects of Invention

According to the invention, the first perimetry is performed on the entire visual field of the subject eye (22a) so as to obtain the threshold testing result (SHR), the probability map image (MAP4) of the pattern deviation probability plot (PDP) is generated from the threshold testing result (SHR), the measurement points (RG) to be used as subsequent measurement points are selected from the abnormal measurement point group of points in which at least a first prescribed number (three) of measurement points (RG) having a P value that is smaller than a first prescribed value (5%) or lower are continuous, and of those, at least one point having the P value that is the second prescribed value (1%) or lower, smaller than the first prescribed value (5%), in the order of the better pattern deviation (PDV) till the number to be selected reaches a prescribed number (10 points). By doing so, since the threshold testing is performed firstly on the entire visual field, the range (RG) where the degree of the disorder is relatively low (the pattern deviation (PDV) is good) and the disorder is likely to progress at higher possibility, that is, the range (RG) where the change of the threshold with a passage of time is easy to be judged in the subsequent inspection is effectively extracted from the ranges (RG) where the P value is small, and the progress of the visual field abnormality is anxious about. And, it is possible to select the measurement points for the subsequent perimetry from the extracted ranges and to store the selected as information of the measurement points of the subsequent perimetry in the memory (13).

At the time of the subsequent perimetry, the information of the measurement points for the subsequent perimetry is read out from the memory (13), the reaction threshold testing is done on the eye (22a) of the examinee only on the measurement points read out. By doing so, it is possible to effectively perform the subsequent perimetry in a short period and in a short time, and to perform the perimetry at higher frequency than as a usual case (three times, for instance, although the perimetry is usually done once on one inspection point) so as to improve the accuracy of the inspection.

Then, it is possible to judge the progress of the disorder, such as Glaucoma, earlier than usual, to lighten the burden on the examinee due to small number of measurement points for the inspection, to inspect each inspection point in detail (at high frequency), and to obtain varied inspection result and to judge the progress earlier.

In a case where a prescribed number of measurement points (10 points) are not selected as the measurement points for the subsequent inspection from only the probability map image (MAP4) of the pattern deviation probability plot (PDP), it is judged that the degree of the visual field abnormality is not so high. Then, it is possible to select the ranges (RG) where the degree of the disorder is relatively high as the measurement points for the subsequent inspection along the running direction of the retina nerve fibers where the visual field abnormality is likely to progress in near future, and to improve the accuracy of the subsequent perimetry in such a way that the sector figure (SEC) that shows sectors divided along the running direction of the retina nerve fibers is referred, and a prescribed number of measurement points are extracted as the measurement points for the subsequent perimetry within the sectors (SC1, SC2, SC3, SC4, SC5, SC6) to which the measurement points (RG) already selected belong, and within the measurement points that are not the abnormal measurement point group, in the order of the worse pattern deviation (in the order of the more serious condition, but the visual field abnormality is not so high) till the selected reaches the prescribed number.

The number in parentheses shows the corresponding element in the drawings for the sake of convenience, accordingly, the descriptions are not restricted and bound by the descriptions on the drawings.

EMBODIMENTS FOR CARRYING OUT THE INVENTION

Embodiments of the invention are mentioned, referring to appended drawings.

Figure 1:
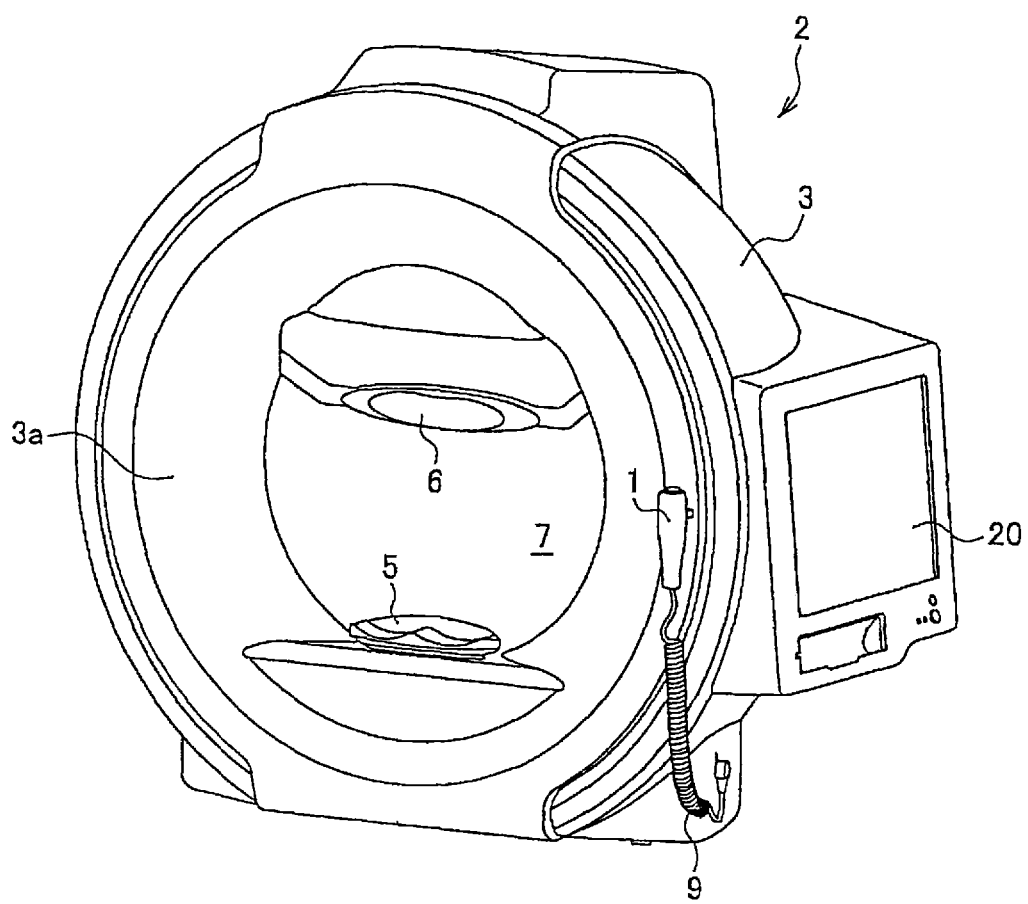
FIG. 1 is a perspective view that shows an example of a perimeter to which the invention is applied.

As shown in FIG. 1, a perimeter 2 has a main body 3 the whole of which is in the shape of a box, and a chin rest 5 and a forehead pad 6 are provided at a front face 3a of the main body 3. A response switch 1 is attachably and detachably located on a right side of FIG. 1 of the main body 3 through a connection flex 9, and a visual field dome 7 in a semi-spherical shape through which stimuli are presented, is provided at a front hand of the chin rest 5 and the head rest 6, that is, inside the main body 3 on a back side of a paper of FIG. 1. The visual field dome 7 is configured so as to project stimulus for perimetry (not shown) at optional positions in the visual field dome 7 through a visual field measurer 10 as shown in FIG. 2 that is built in the main body 3.

Figure 2:
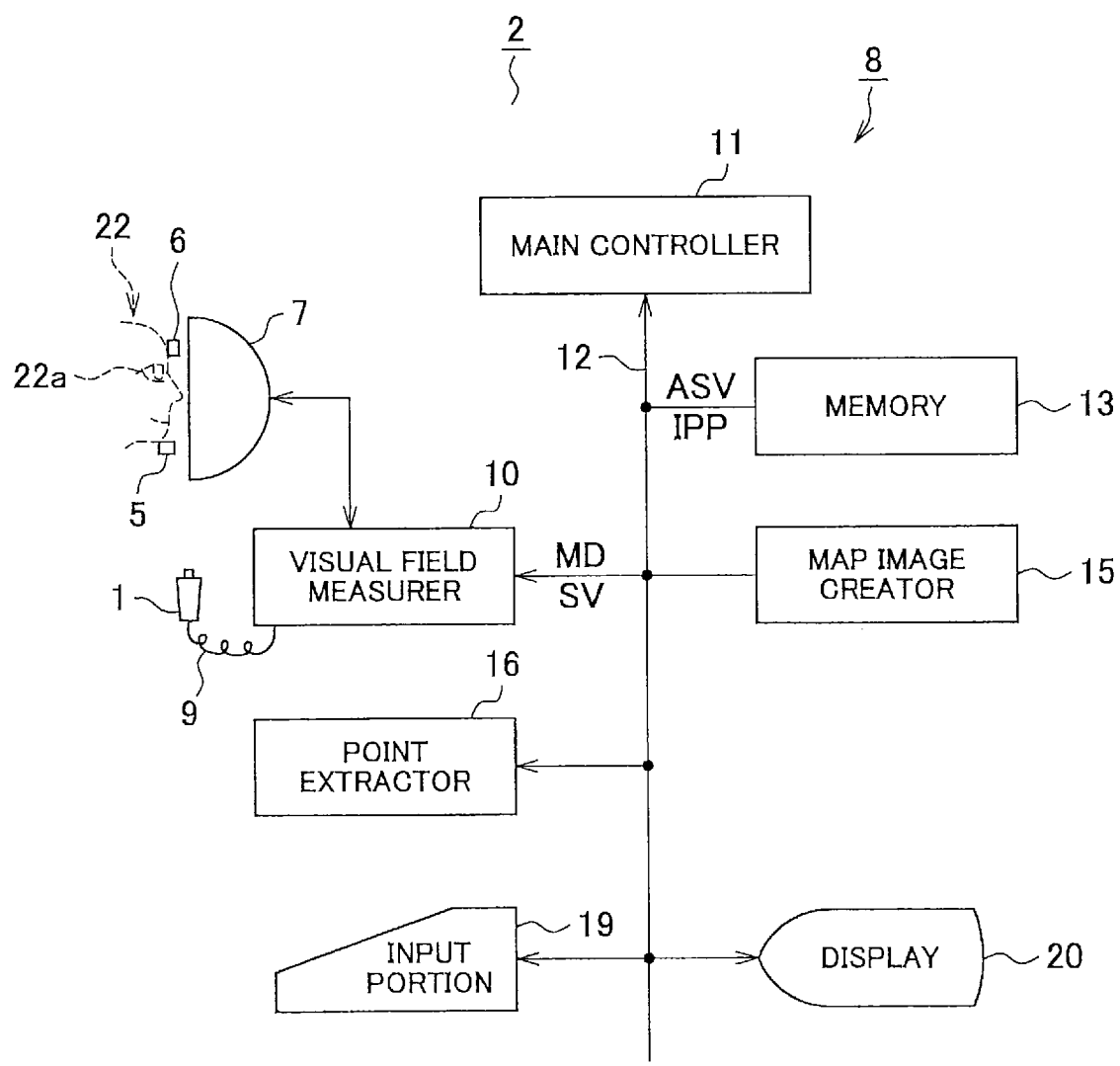
FIG. 2 is a control block diagram that shows an example of control portions of the perimeter of FIG. 1.

Besides, as shown in FIG. 2, a controller 8 of the perimeter 2 is provided inside the main body 3, and the controller 8 has a main controller 11. A memory 13, the above-mentioned visual field measurer 10, a map image creator 15, a point extractor 16, an input portion 19, such as a keyboard, and a display 20 are connected with the main controller 11 via a bus line 12. A control block diagram as shown in FIG. 2 shows only portions that relate to the invention and does not show the other constitutional portions of the perimeter 2 that are not related to the invention.

The perimeter 2 has the above-mentioned structure. In order to measure a visual field of subject eyes 22a of an examinee 22 so as to use for diagnoses for a glaucoma and the like, an examinee is invited to put his (her) chin on the chin rest 5 and to contact his (her) forehead with the head rest 6 so as to be pressed against such a pad such that the subject eye 22a of the examinee 22 is located at a predetermined perimetry position, as shown in FIG. 2.

Figure 3:
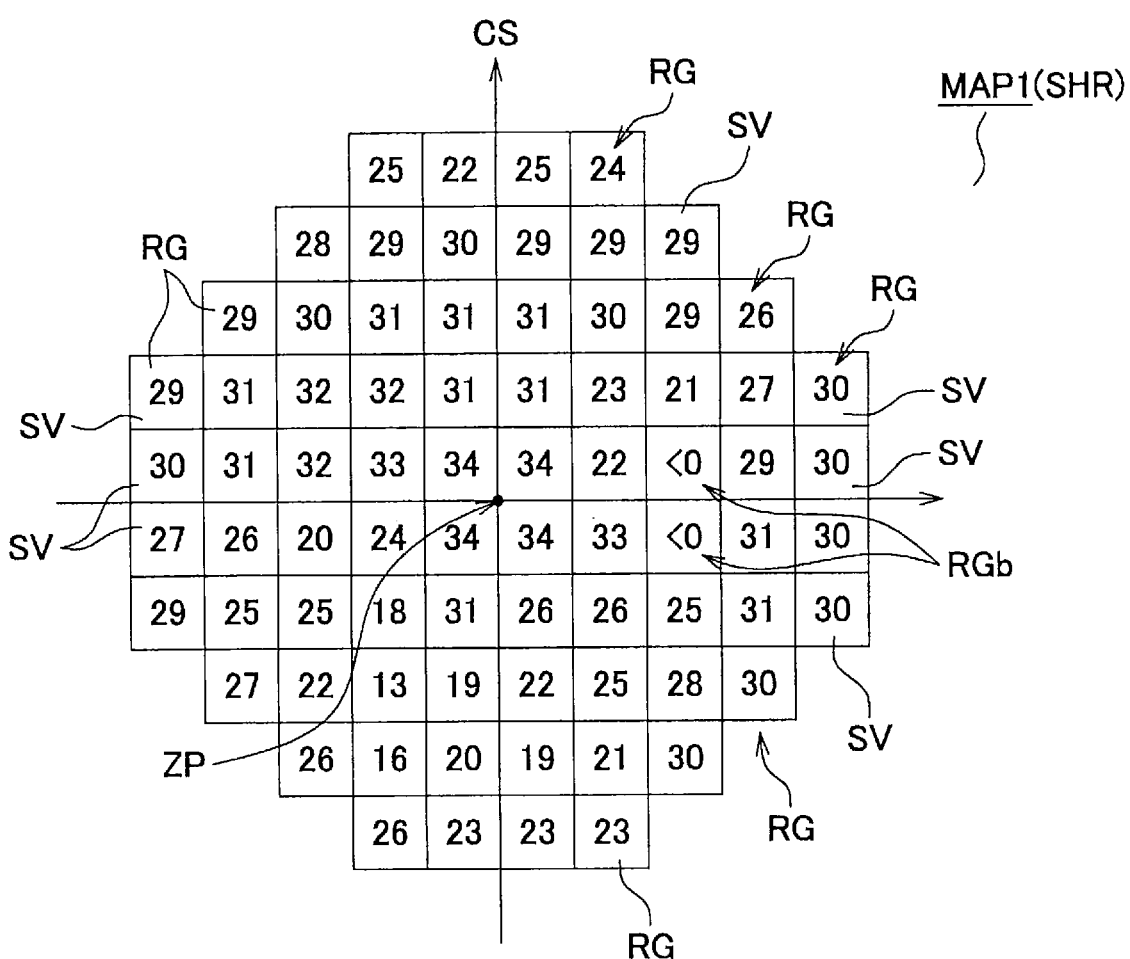
FIG. 3 is a map image of a threshold inspection result of a perimetry on a subject eye.

When an operator instructs the perimeter 2 to start a visual field measurement operation through the input portion 19 in the afore-mentioned state, the main controller 11 instructs the visual field measurer 10 to measure the visual field of the subject eye 22a. Receiving such an instruction, the visual field measurer 10 presents the stimuli (not shown) in order at proper positions inside the visual field dome 7 with a well-known method of the perimetry. At the results, as shown in FIG. 3, minimum values of brightness of the stimuli to which the examinee can respond regarding two or more measurement points (for instance, 50 measurement points or more, such as 54 points, and 76 points, which are indicated with many square ranges RG in the figure and are set, corresponding to an entire range of a retina of a fundus, that is, the entire range of the visual field) on a measurement coordinate system CS are measured and collected, and these values, threshold SV (dB), are indicated on the display 20 with numeral numbers as a map image MAP1 and are stored in the memory 13. As a method of obtaining the threshold SV, it is sufficient to adopt a value corresponding to a response result to the stimuli presented to the examinee 22 with various brightness. Otherwise, the other methods may be adopted. One method is to collect the response reaction to the light spots (the stimuli) to be presented to the examinee 22 with various brightness and to estimate the threshold SV (dB) from such a response reaction. The map image MAP1 is comprised of two or more ranges RG (50 ranges or more, such as 54 ranges and 76 ranges) that correspond to the above-mentioned measurement points. An origin ZP of the measurement coordinate system CS in the figure that is used for the perimetry is set, corresponding to a center position of a macula of the subject eye 22a, and a portion where the threshold SV<0 in the figure is a point (a range) to which the examinee does not respond (to which the examinee is not able to perceive). In case of FIG. 3, the measurement points that correspond to the ranges RG are ones that correspond to blind spots. The range RG (not shown) indicated as the threshold "0 (zero)" means that the examinee perceived the stimulus having 0 dB brightness.

When the examinee perceives the stimulus presented on the visual field dome 7 through the subject eye 22a at the time of the perimetry, he (or she) operates the response switch 1. If not perceived, the examinee does not operate the response switch 1. So, it is possible for the visual field measurer 10 to obtain the measurement results regarding the respective measurement points, as shown in FIG. 3, relating the state of the operation of the response switch 1 and the position and the brightness of the stimulus inside the visual field dome 7 at this time to each other. In the measurement results of FIG. 3, the value of the threshold SV is a reaction threshold of the subject eye 22a, and the measured result is referred to as threshold testing result SHR for this reason.

After thus obtaining the threshold testing result SHR regarding the subject eye 22a, the main controller 11 instructs the map image creator 15 to compute a total deviation and a pattern deviation regarding each measurement point of the obtained threshold testing result SHR and to display a total deviation result THR and a pattern deviation result PHR.

Figure 4:
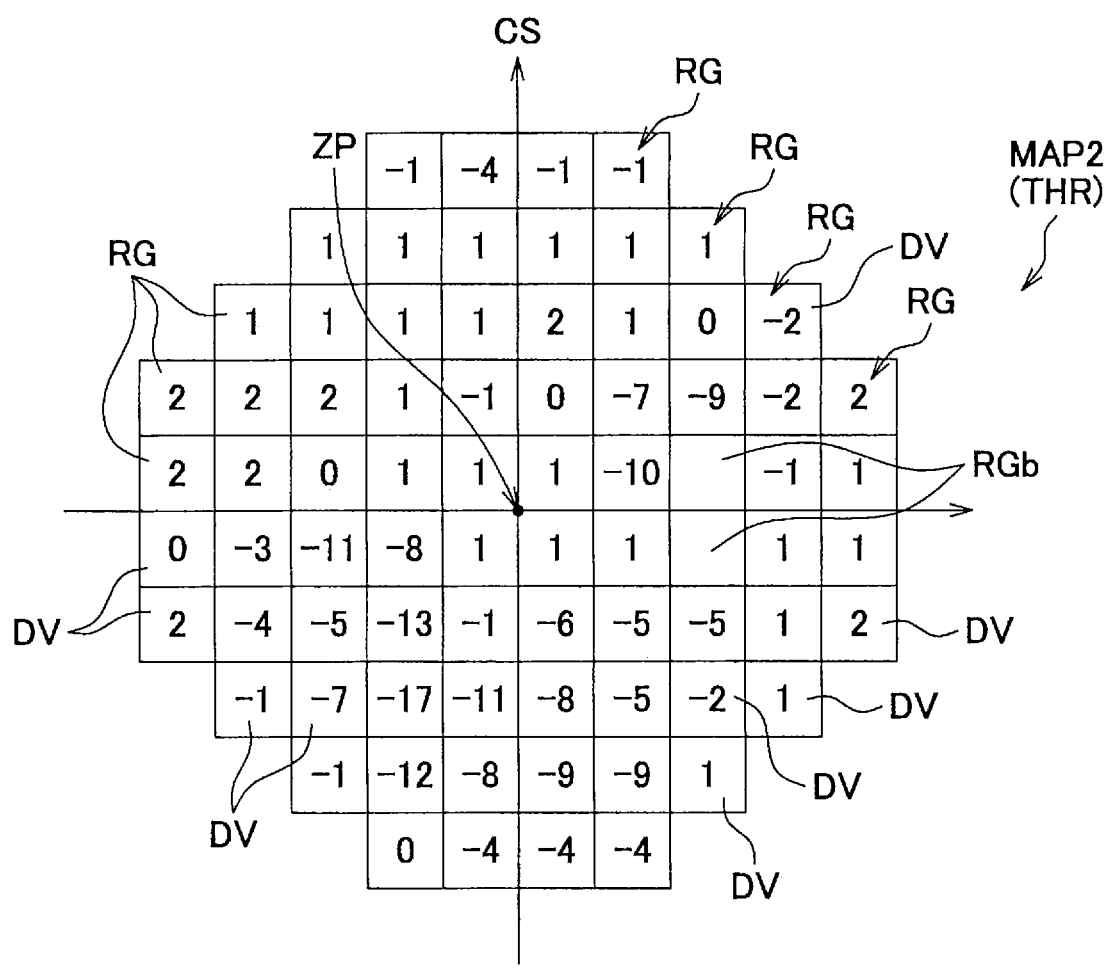
FIG. 4 is a map image of a total deviation with regard to the threshold inspection result of the perimetry on the subject eye.

For the total deviation result THR, the map image creator 15 reads a normal threshold ASV regarding each measurement point of the perimetry out of the memory 13 and obtains a difference between the threshold SV actually measured and the normal threshold ASV as a total deviation DV (dB), and generates a map image MAP2 on which the deviation value DV regarding each measurement point is indicated as shown in FIG. 4, corresponding to a fundus visual field range and indicates this image on the display 20. In such a case, the normal threshold ASV may be a mean value of the measurement results of many subject eyes, or may be proper value, such as a median of the measurement results of the subject eyes since it is the threshold that is regarded as the normal value in each measurement point. The total deviation DV is a difference between a normal sensitivity curve NS indicated with the normal threshold ASV and the threshold SV actually measured as the measurement result of the subject eye 22a, as shown in FIG. 9.

In the map image MAP2 of the total deviation result THR of FIG. 4, the range RG on which "0" is indicated as the total deviation value DV is the measurement point in which the measured threshold SV and the normal threshold ASV are equal to each other, and the range RG on which a positive number, such as "1" and "2", is indicated is the measurement point in which the measured threshold SV is higher than the normal threshold ASV in the sensitivity, and the range RG on which a negative number, such as "−1" and "−2", is indicated is the measurement point in which the measured threshold SV is lower than the normal threshold ASV in the sensitivity. The obtained threshold testing result SHR, the total deviation result THR, and their map images MAP1 and MAP2 are respectively stored in the ranges in the memory 13, attaching ID data corresponding to the subject eye 22a thereto as measurement data of the subject eye 22a of the examinee 22.

Figure 9:
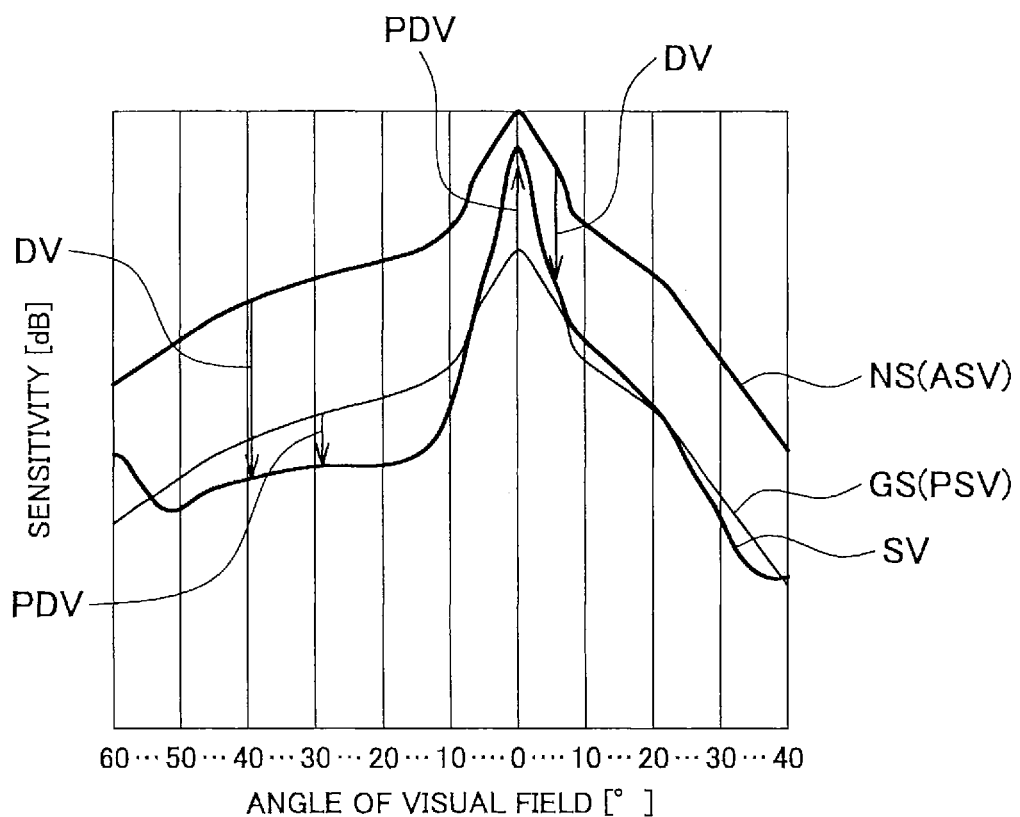
FIG. 9 is a view showing a relation between the total deviation and the pattern deviation.

Besides, for the pattern deviation result PHR, the map image creator 15 reads the threshold SV of the subject eye 22a on each measurement point (each region RG) of the perimetry from the memory 13, and obtains a normal visual field pattern GS that corresponds to a sensitivity level of the subject eye 22a computed and estimated from the threshold SV as an estimated threshold PSV for each measurement point (each region RG) with a well-known method as shown in FIG. 9. In such a case, the estimated threshold PSV may be stored in the memory 13, corresponding to the measurement result of the subject eye 22a in such a manner the normal threshold ASV is amended in association with the sensitivity level (threshold) of each measurement point. A difference between the estimated threshold PSV obtained for each measurement point (each region RG) and threshold SV actually measured is a pattern deviation PDV (dB). That is, the pattern deviation PDV is a value that indicates a partial disorder of the visual field that is obtained in such a way that the normal value data amended according to the age of the examinee is subtracted from the threshold measured through the perimeter, and the total deviation representing thus obtained value is amended in consideration of the depression or the rise of the entire visual field.

Figure 5:
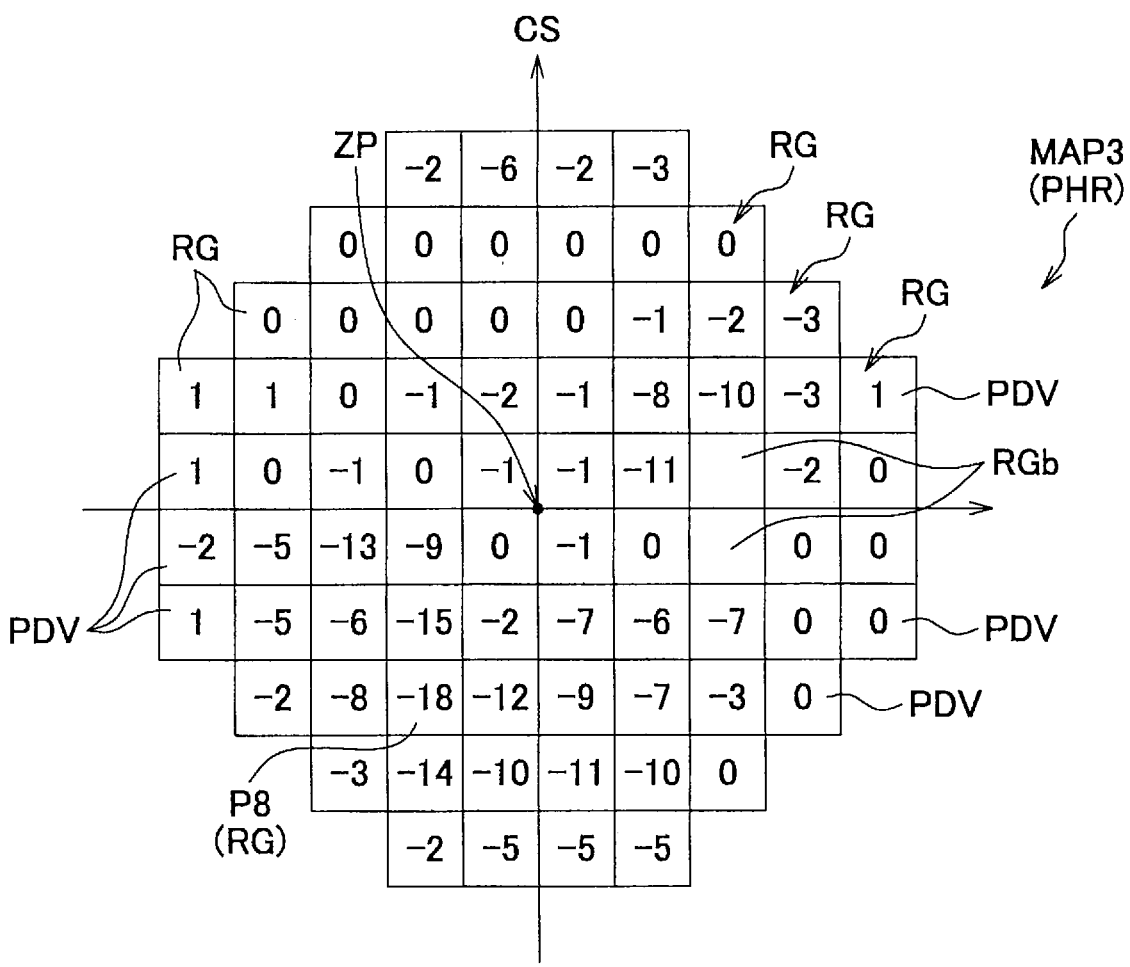
FIG. 5 is a map image of a pattern deviation with regard to the threshold inspection result of the perimetry on the subject eye.

This is a procedure for detecting the partial disorder of visual field that is difficult to be judged in the total deviation with the normal threshold ASV in such a way that a depression or a rise of the entire visual field is amended by the estimated threshold PSV that corresponds to a lowering or a rise of the sensitivity of the subject eye 22a which is indicated by the threshold SV of the subject eye 22a actually measured. The map image creator 15 computes the difference between the measured threshold SV of the subject eye 22a on each measurement point and the estimated threshold PSV as the pattern deviation PDV, indicates the values PDV, corresponding to the ranges RG of the fundus on the respective measurement points so as to create a map image MAP3 and displays such a map on the display 20 as shown in FIG. 5. In the map image MAP3 of the pattern deviation result PHR of FIG. 5, the range RG where the pattern deviation PDV is "0" is the measurement point where the measured threshold SV and the estimated threshold PSV is equal, the range RG where a positive number, such as "1" and "2", is indicated is the measurement point where the sensitivity of the measured threshold SV is higher than one of the estimated threshold PSV, and the range RG where a negative number, such as "−1" and "−2", is indicated is the measurement point where the sensitivity of the measured threshold SV is lower than one of the estimated threshold PSV. The obtained pattern deviation result PHR and its map image MAP3 are stored in a range attaching ID data corresponding to the subject eye 22a in the memory 13 as the measurement data MD of the subject eye 22a of the examinee 22.

After thus finishing the first perimetry on the subject eye 22a, the operator instructs the main controller 11 to extract the inspection points to be used in the subsequent perimetry through the input portion 19 on the basis of the map image MAP1 of the threshold SV, the map image MP2 of the total deviation result THR and the map image MAP3 of the pattern deviation result PHR on the subject eye 22a that are stored in the memory 13. Receiving such an instruction, the main controller 11 instructs the point extractor 16 to extracts 10 inspection points to be used in the subsequently perimetry.

The point extractor 16 reads a point extracting program IPP out of the memory 13, and starts to extract the inspection points to be used in the subsequent perimetry. According to the invention, it is possible to judge a degree of the progress of the disorder, such as the Glaucoma, earlier than in a conventional case in such a manner that the inspection is effectively executed in a short time only on the inspection points that are anxious about the progress of the disorder on the basis of the normal perimetry results, and the inspection is done at a higher frequency than in a conventional case (for instance, the inspection is done three times on one inspection point in order to improve the accuracy of the inspection although the inspection is generally done once). Besides, the inspection points are few and each inspection point is inspected in details (at a higher frequency) as mentioned above, so that it is possible to obtain uneven inspection results and to quickly judge progress of the disorder.

For instance, an aim is to select 10 points that are anxious about the progress of the disorder from the inspection result of 54 through 76 points, to do the inspection once a month and to judge the progress of the disorder within half a year. Then, the aim of the point extracting program IPP is to largely reduce the inspection points to be inspected in the subsequent perimetry from the number of the measurement points in the first normal perimetry (In a case of FIG. 3, 76 measurement points are set on each subject eye 22a) and to extract effective and sufficient 10 points from the first normal perimetry results, for instance.

Figure 6:
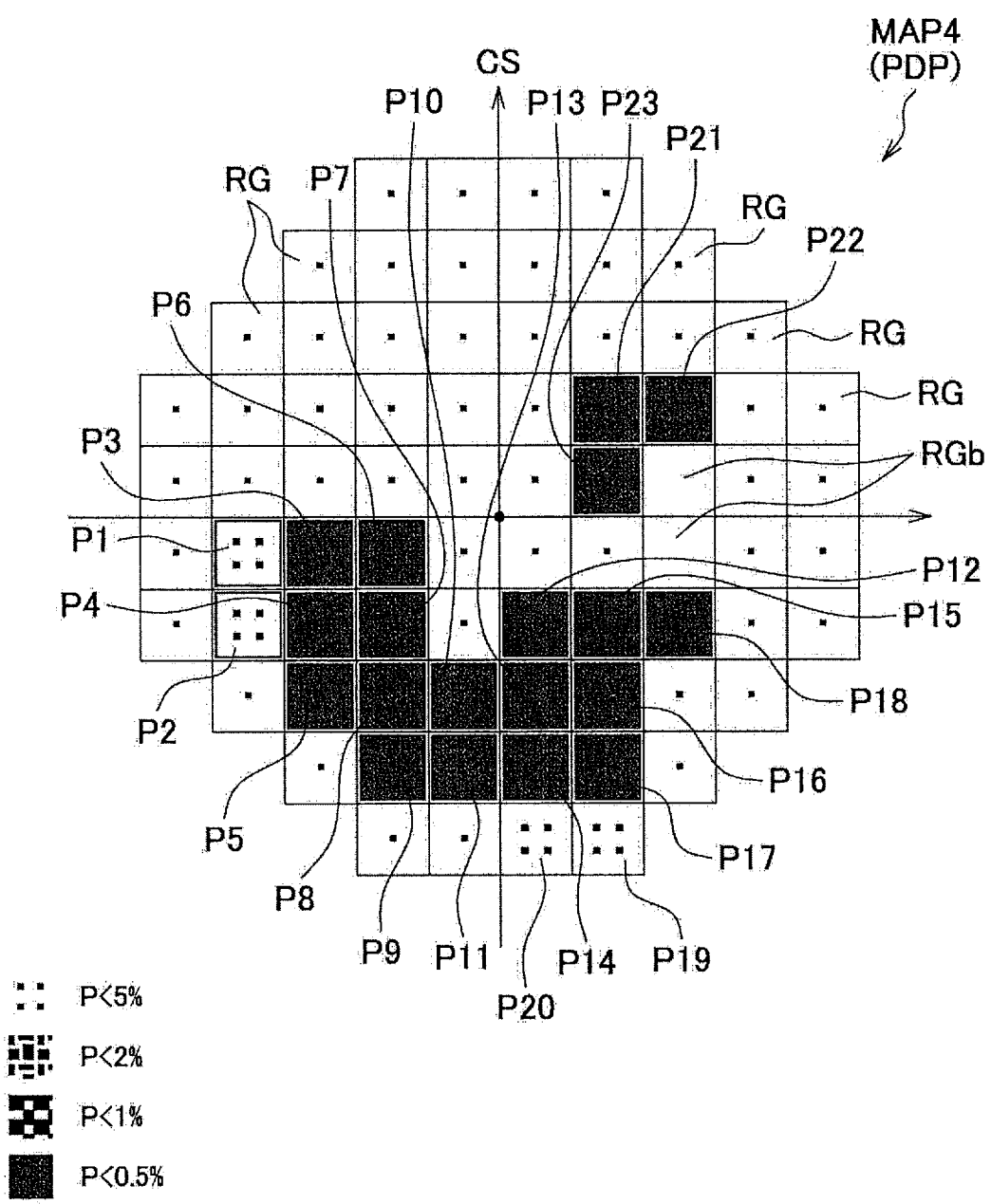
FIG. 6 is a map image of a pattern deviation probability plot with regard to the threshold inspection result of the perimetry on the subject eye.
Figure 8:
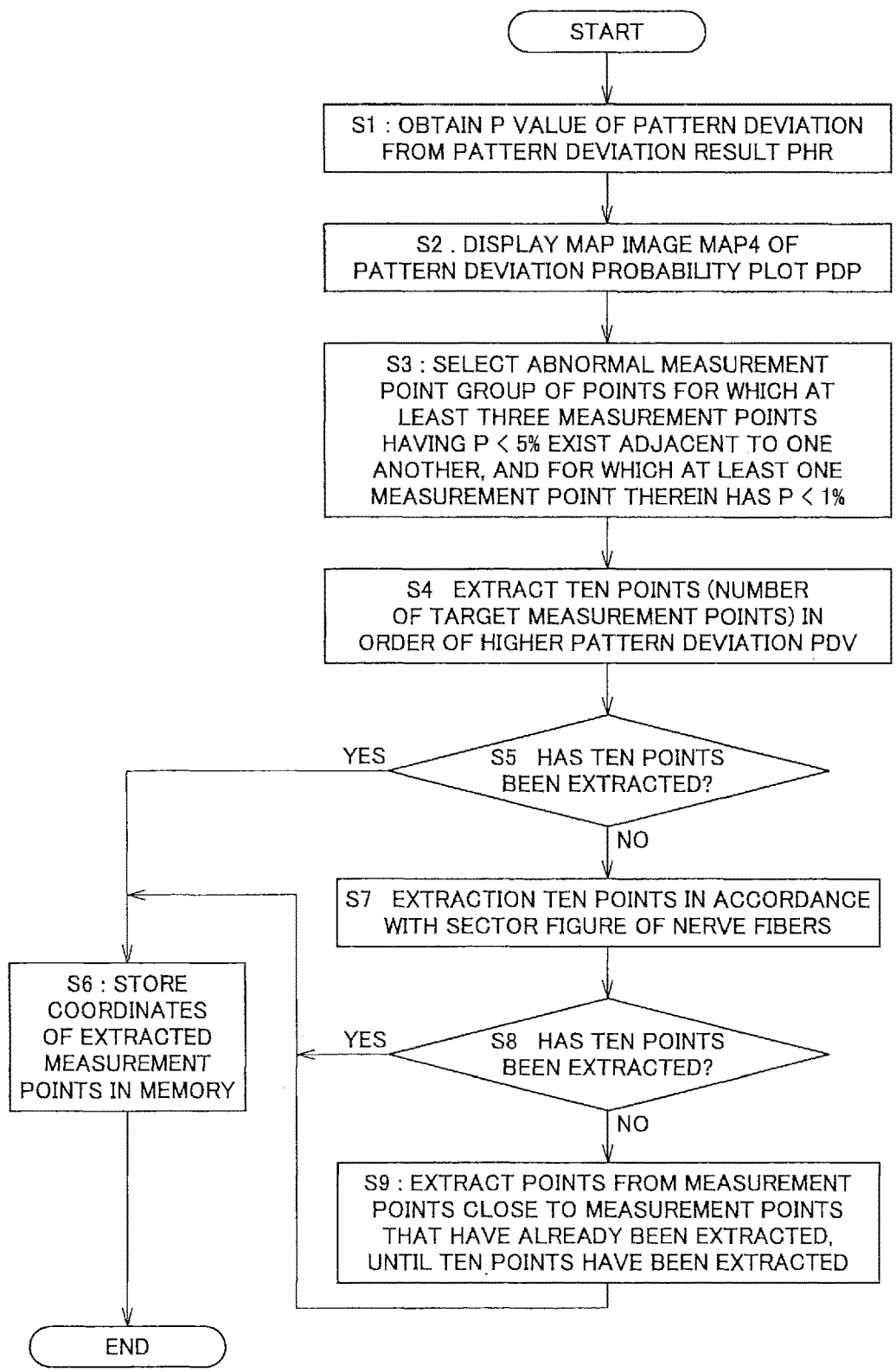
FIG. 8 is a flowchart that shows an example of point extracting program.

The point extractor 16 obtains a P value (probability) that represents each pattern deviation PDV of the pattern deviation result PHR of the subject eye 22a that was obtained in FIG. 5 as a probability variable in Step S1 of the point extracting program IPP as shown in FIG. 8, and produces a map image MAP4 comprised of pattern deviation probability plot PDP as shown in FIG. 6 and displays such a map on the display 20 in Step S2. In the pattern deviation probability plot PDP, the respective ranges RG are divided into four stages of P values, P<5%, P<2%, P<1% and P<0.5%, and it is judged that the lower the P value is, the higher the degree of an abnormality of the threshold SV is, that is, the degree of the abnormality of Glaucoma is making a progress. As shown in an explanation of FIG. 6, the respective ranges RG (measurement points) are divided into four stages as patterns according to the P value, and each range RG (measurement point) is filled with black color as the P value becomes lower. In a case where the P value is 5% or higher, it is judged the degree of the abnormality of the threshold SV is low, so that such a range is indicated with one black point in FIG. 6 (such an range is excluded from the four stages).

After the pattern deviation probability plot PDP is thus indicated with the map image MAP4, the point extracting program IPP enters Step S3, and the point extractor 16 selects an abnormal measurement point group (range RG group) where there are three measurement points or more having the P value that is lower than 5%, being adjacent to one another, excluding the ranges RG of the most peripheral portion, and at least one of these is P<1%. Such a selection criterion is well-known as the criterion of visual field abnormality of Glaucoma by Anderson, but it is not necessary to always use such a criterion. The abnormality measurement point group (the range RG group) may be extracted and selected where there continuously exist a prescribed numbers of measurement points (the ranges RG) or more each of which P value is a first prescribed value or lower, and at least one of these points is a second prescribed value or lower, that is smaller than the first prescribed value.

In a case of FIG. 6, there are two abnormality measurement point groups (the range RG group), P1 through P18 and P21 through 23, where there adjacently exist three ranges which P values are lower than 5% and at least one of these ranges which P value is lower than 1%. In such a case, the measurement points (the ranges RG) P19 and P20 are ones of the visual field which are the most peripheral portion, so that these are excluded from the abnormal measurement point group even if the P value is lower than 5%. Then, in Step S3, two abnormal measurement point groups, the points P1 through P18 and P21 through P23 are extracted as inspection point candidates.

Subsequently, the point extracting program IPP enters Step S4, and the point extractor 16 extracts the ranges RG in the order of the higher pattern deviation PDV (the better inspection result) from the extracted two abnormal measurement point groups, referring to the pattern deviation result PHR of FIG. 5 until the measurement points to be measured in the subsequent perimetry reaches target number of inspection points. In this embodiment, the measurement points are extracted up to ten points that are a one-fifth or lower regarding 50 measurement points or more (the ranges RG) that are set on the perimeter, corresponding to a fundus.

The extraction of the ranges RG in the order of the higher pattern deviation PDV means the extraction of the ranges RG in the order of the better result of the pattern deviation PDV (but, the P values of such points are P<5% as shown in Step S3, so that the disorder of the visual field clearly exists), that is, the extraction in the order of the few visual field abnormality. This is to extract the points judged that the disorder does not so progress at high probability, that is, the visual field abnormality is likely to progress in near future, of the points (the ranges RG) where the visual field abnormality exist, and such a point is the important in order to judge the visual field abnormality in a short period. For instance, the pattern deviation PDV of the range RG of the point P8 of the pattern deviation result PHR of FIG. 5 is "−18", and it is known that the pattern deviation value PDV is extremely lower in comparison with the other points P1 through P18 and points P21 through P23. It is estimated that the visual field abnormality considerably progresses in such a range RG. On the contrary, the abnormality is less likely to progress more (to turn worse) in future, and even if the threshold SV in such a range RG is measured with a passage of time, its change is small and such a measurement does not conform to the purpose of the invention for diagnosing the visual field abnormality in a short period. Therefore, it is not preferable such a measurement point P8 is extracted and selected as the subsequent inspection measurement point.

In a similar meaning, in the ranges RG where DV≤−20 (dB) (concrete numeral value can be properly set) that is known by referring to the total deviation result THR of FIG. 4 at the time of extracting the measurement points in Step S4, the blind spots are deep, and it is predicted that the disorder is hard to progress in such points (that is, it is difficult to diagnose the progress of the visual field abnormality in a short period), so that these points may be excluded from the procedure of extracting the measurement points.

Subsequently, the point extracting program IPP enters Step S5 and the point extractor 16 judges whether the target number of inspection points to be extracted from the measurement points (ranges RG) reaches a prescribed number (in this case, 10 points).

In a case where such an extraction of 10 measurement points (the ranges RG) is finished in Step S4, the program enters Step S6 and coordinates of the extracted measurement points (the ranges RG) are stored in the memory 13 as the measurement points in next perimetry.

In a case where 9 measurement points (the ranges RG) or lower (including zero point) are extracted in Step S4, the program enters Step S7, and a sector figure SEC that shows the measurement point group associated with an running direction of the retina nerve fibers is read out from the memory 13, and by referring to the sector figure SEC, the measurement points included in the same sector are extracted as a shortage from the inspection points excluding the abnormal measurement point group in the measurement points already extracted in the order of the lower (the worse) pattern deviation value PDV till the measurement points reaches 10 points.

Figure 7:
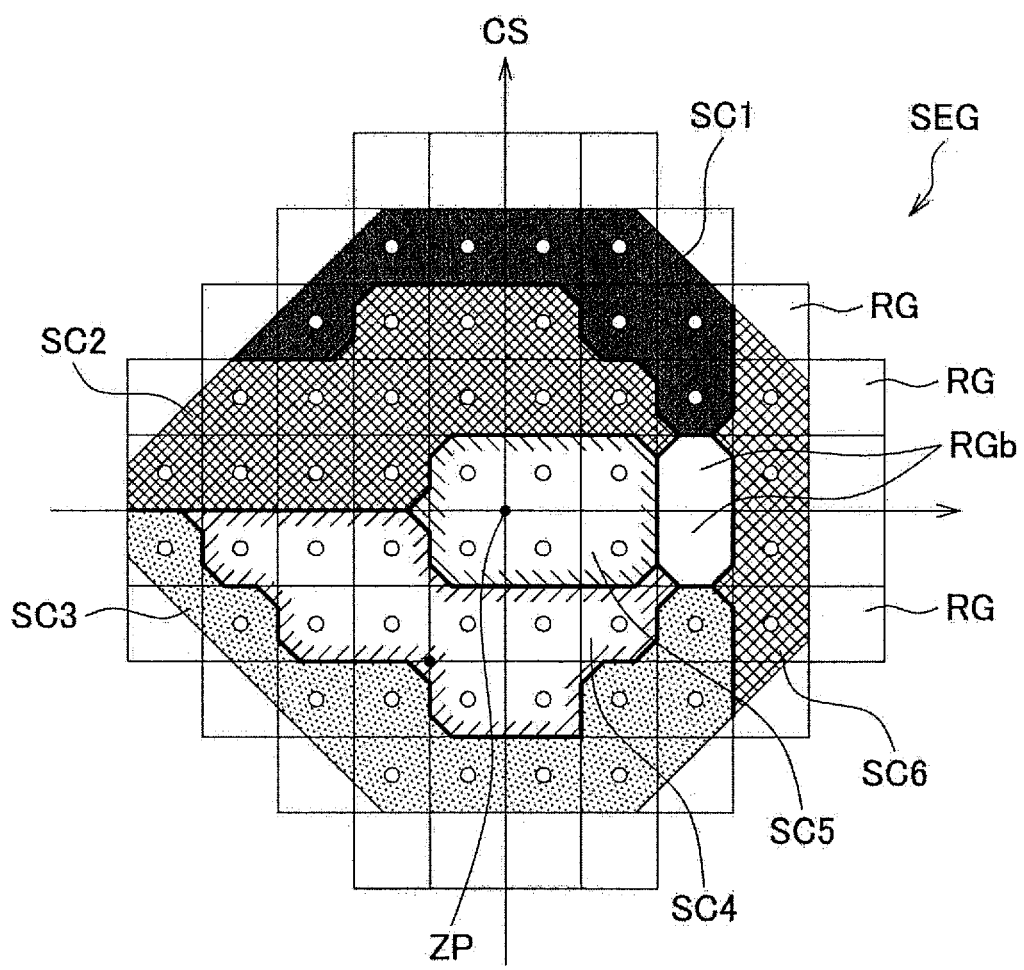
FIG. 7 is a map image that shows inspection point sectors.

The sector figure SEC has sectors made by dividing the respective ranges RG (the measurement points) of the visual field to be measured of measurement coordinates CS, corresponding to a running of retina nerve fibers of the fundus as shown in FIG. 7, and in the case of FIG. 7, the respective regions are divided into 6 ranges, sectors SC1, SC2, SC3, SC4, SC5 and SC6 according to the running direction of the retina nerve fibers (blind point regions RGb are excluded). A lesion of the visual field abnormality, such as the Glaucoma, is more likely to progress along the running direction of the retina nerve fibers, so that the measurement points in the sectors to which the measurement points (the ranges RG) already extracted in Step S4 belong are extracted from the inspection points excluding the abnormal measurement point group in the order of the lower (the worse) pattern deviation PDV till the measurement points reach 10 points.

If the 9 measurement points (the ranges RG) or lower are extracted in Step S4, it is judged that the degree of the visual field abnormality is not so high. Therefore, it is possible to properly detect the progress of the visual field abnormality at the subsequent perimetry with high possibility in such a way that the measurement points (the ranges RG) are extracted from ones along the running direction of the retina nerve fibers where the visual field abnormality is likely to progress in future, that is, from ones in the sectors to which the measurement points (ranges RG) already extracted belong excluding the abnormal measurement point group in the order of the lower (the worse) pattern deviation PDV in Step S7.

After finishing the extraction of the measurement points along the sector figure SEC in Step S7, the point extractor 16 judges in Step S8 of the point extracting program IPP whether the target number of the measurement points (the ranges RG) to be extracted reaches a prescribed number (in this case, 10 points).

When the 10 measurement points (the ranges RG) has been extracted in Step S7, the program enters Step S6 and the coordinates of the extracted measurement points (the ranges RG) are stored in the memory 13 as the measurement points in the next perimetry.

If the 9 measurement points (the ranges RG) or lower are extracted in Step S7, the point extracting program IPP enters Step S9 and the point extractor 16 selects and extracts the measurement points from the ranges RG close to the measurement points (the ranges RG) already extracted in the order of the range RG closer to the measurement points (the ranges RG) already extracted on the map image MP4 of the pattern deviation probability plot PDP till the number of the measurement points reaches 10. When extracting the measurement points (the ranges RG) close to ones having the low (bad) pattern deviation PDV from the measurement points already extracted, it is possible to extract the measurement points where the visual field abnormality progress in future with high probability.

When finishing the extraction of the 10 measurement points (the ranges RG) in Step S9, the program enters Step S6 and the coordinates of the extracted measurement points (the ranges RG) are stored in the memory 13 as the measurement points at the subsequent perimetry and the procedure of extracting the inspection points through the point extractor 16 finishes.

After finishing the extraction of a prescribed number of measurement points (the ranges RG) (10 points in this embodiment) to be used at the subsequent perimetry through the point extractor 16, the subsequent perimetry is done on the examinee every one month, for instance. This inspection interval is largely short in comparison with half a year or one year in a case of the normal perimetry, but it is sufficient to perform the subsequent perimetry on only 10 points extracted according to the point extracting program IPP of the 76 measurement points, for instance as shown in FIG. 3, without performing the inspection on all measurement points (the ranges RG) in the visual field dome 7. Then, it is possible to repeat the perimetry in a short period without an excessive burden on the examinee.

When inputting the identification code, such as a ID of the examinee, through the input portion 19 at the subsequent perimetry, a prescribed number of measurement points (the ranges RG) (in this case, 10 points) (the measurement points in the subsequent perimetry) extracted according to the point extracting program IPP are read out of the measurement result of the first perimetry for the subject eye 22a of the examinee stored in the memory 13 and the read is outputted on the display 20 or a printer (not shown) as re-inspection points, so that it is possible for the examiner to immediately measure the thresholds SV for the re-inspection points by presenting the stimuli in the visual field dome 7 on such re-inspection points only. The visual field measurer may perform this re-inspection through automatically presenting the stimuli on the re-inspection points in order so as to obtain the thresholds SV.

Although it is necessary to inspect the whole ranges RG of the visual field as usual in the first perimetry, according to the invention, the pattern deviation result PHR is acquired from the perimetry result, the P value (probability) that represents each pattern deviation PDV as a probability variable comprising the pattern deviation result PHR is obtained, the pattern deviation probability plot PDP as shown in FIG. 6 is generated, a target number of inspection points where the visual field abnormality seems to progress are extracted from these values according to the point extracting program IPP, and the extracted inspection points are stored in the memory 13 as information of the measurement points at the subsequent perimetry. And, at the time of the subsequent perimetry, the main controller 11 reads the information of the measurement points for the subsequent perimetry stored in the memory, and perform the inspection of the reaction threshold only on the measurement points on the subject eye 22a of the examinee. By doing so, it is possible to effectively perform the subsequent perimetry in a short period and in a short time, and at a higher frequency than an usual case (for instance, the inspection generally is done once on one inspection point, but the inspection is done three times in order to improve the inspection accuracy).

Then, it is possible to judge the progress of the disorder, such as Glaucoma, earlier than usual, to inspect each inspection point in detail (at high frequency) due to small number of the inspection points, and to obtain varied inspection result and to judge the progress earlier.

In some cases, the inspection points are concentrated on a part of the fundus visual field range since the inspection points are few in the perimetry of the invention. In such a case, the examinee may predict that the stimulus appears on some range and may concentrate his (her) consciousness to such a range, so that its fixation state may be worse and the result different from the usual perimetry may be brought. If the inspection point is thus concentrated on a part of the range, it is possible to obtain the result similar to the usual perimetry in such a way that luminous points similar to the inspection points at the time of the inspection are presented to the range having no inspection point as dummy stimuli (the luminous points may be set brighter than the usual inspection) in order not to concentrate the examinee's consciousness to a part to the range.

If the inspection points are concentrated to a part of the range due to the result of selection of the inspection points, the entire visual field may be divided into four quadrants, for instance. If the inspection points are concentrated to some quadrant, or if there is the quadrant having no inspection point, the dummy stimulus may be presented to the quadrant having no inspection point with a certain probability.

EXPLANATION OF REFERENCE NUMBERS

2 . . . perimeter
11 . . . main controller (display)
13 . . . memory
15 . . . pattern deviation calculator, probability map producer (map image creator)
16 . . . measurement point selector, sector extractor, map image selector (point extractor)
19 . . . input portion (input portion)
20 . . . display
21 . . . examinee
22a . . . subject eye
RG . . . measurement point (range)
SC1, SC2, SC3, SC4, SC5, SC6 . . . sector
SV . . . threshold
PDP . . . pattern deviation probability plot
PDV . . . pattern deviation
SEC . . . sector figure
SHR . . . threshold inspection result
MAP1, MAP2, MAP3, MAP4 . . . map image

What is claimed is:

1. A perimeter capable of acquiring, as a threshold, or value corresponding to a response result of an examinee to a stimulus presented with various brightness, for a set of measurement points of a first number set across an entire visual field of the ocular fundus of a subject eye, displaying the threshold as a map image of a threshold testing result and storing the threshold in a memory, the perimeter comprising:
the measurement points of the first number comprising a plural number of regions and the map image showing the threshold at each of the measurement points in each of the corresponding regions;
an estimated threshold calculator that obtains a normal visual field pattern corresponding to a sensitivity level of the subject eye estimated from the threshold as an estimated threshold for each of the regions, from the threshold for each of the measurement points for the threshold testing result;
a pattern deviation calculator adapted to obtain a difference between the estimated threshold obtained for each of the measurement points and the threshold of the subject eye to define an obtained pattern deviation;
a probability map producer adapted to obtain a P value representing the obtained pattern deviation for each of the measurement points as a probability variable, and to generate a probability map image of a pattern deviation probability plot indicating the measurement points for respective ones of the P values;
a measurement point selector adapted to determine a subset of measurement points from the set of measurement points, the subset corresponding to abnormal measurement point groups, to define subsequent measurement points the subset consisting of a prescribed number of points which is less than the first number, the subsequent measurement points adapted to be used in a subsequent perimetry limited to the subsequent measurement points, the abnormal measurement point groups having measurement points having a P value that is at most a first prescribed value, and the regions of the measurement points of the abnormal measurement point groups being adjacently and continuously existing, and numbering more than a prescribed number in the probability map image, with the result that at least one of the measurement points of the subset of the abnormal measurement point groups has another P value that is a second prescribed value less than or equal to the first prescribed value, and;
a memory that stores the subsequent measurement points selected through the measurement point selector;
wherein the selection of the subsequent measurement points through the measurement point selector is controlled in such a way that the measurement points are selected from the measurement points comprising the abnormal measurement point groups in order of the measurement points having a higher pattern deviation.

2. The perimeter according to claim 1, further comprising:
an input means through which an identification code on the subject eye can be inputted, and a re-inspection measurement point output means that, when the identification code is inputted in the input means, reads the subsequent measurement points for the subject eye corresponding to the identification code out of the memory and outputs the read out to the output means.

3. The perimeter according to claim 1, wherein the memory stores a sector figure that shows sectors formed by dividing the visual field to be measured so as to correspond to a running direction of retina nerve fibers, and the measurement point selector has a sector extractor, the sector extractor reads and refers to the sector figure stored in the memory when the number of selecting the subsequent measurement points through the measurement point selector does not reach the prescribed number, and extracts from the measurement points the subsequent measurement points in the order of a lower pattern deviation to define an extracted number of measurement points that reaches the prescribed number.

4. The perimeter according to claim 1, wherein the prescribed number is 10.

5. The perimeter according to claim 1, wherein the measurement point selector has a map image selecting means, wherein when the number of selecting the subsequent measurement points through the measurement point selector does not reach the prescribed number, the map image selecting means selects one of the regions in which measurement points were not selected from the abnormal measurement point group in the probability map image by order of shorter distance from a region of measurement points already selected as one of the subsequent measurement points.

6. The perimeter according to claim 1, wherein the measurement point selector selects from the abnormal measurement point group in the probability map image, the measurement points, in which at least a prescribed number of the regions of the measurement points have a respective P value as a probability variable that is 5% or lower, are continuous as the subsequent measurement points, and in which the P value of at least one of the measurement points is 1% or lower.

7. The perimeter according to claim 6, wherein the measurement point selector selects, from the abnormal measurement point group in the probability map image, the measurement points in which at least three regions of the measurement points have the P value as a probability variable that is 5% or lower, are continuous to subsequent measurement points, and the P value of at least one of the measurement points is 1% or lower.

* * * * *